United States Patent
Jablons

(10) Patent No.: US 8,684,005 B2
(45) Date of Patent: Apr. 1, 2014

(54) NASAL CANNULA ASSEMBLY

(75) Inventor: Mitchell L. Jablons, Watchung, NJ (US)

(73) Assignee: Jemi Airway Management LLC, New York, NY (US)

( * ) Notice: Subject to any disclaimer, the term of this patent is extended or adjusted under 35 U.S.C. 154(b) by 177 days.

(21) Appl. No.: 12/717,471

(22) Filed: Mar. 4, 2010

(65) Prior Publication Data
US 2010/0224196 A1 Sep. 9, 2010

Related U.S. Application Data

(60) Provisional application No. 61/157,440, filed on Mar. 4, 2009.

(51) Int. Cl.
*A61M 15/08* (2006.01)
*A61M 31/00* (2006.01)

(52) U.S. Cl.
USPC .................................. 128/207.18; 604/94.01

(58) Field of Classification Search
USPC ............. 128/207.18, 206.25, 207.13, 204.12, 128/200.26, 203.22, 206.11, 203.29, 128/204.11, DIG. 26; 604/94.01, 389, 391, 604/275
See application file for complete search history.

(56) References Cited

U.S. PATENT DOCUMENTS

| 4,278,082 | A | 7/1981 | Blackmer |
| 5,682,881 | A | 11/1997 | Winthrop et al. |
| 6,807,967 | B2 | 10/2004 | Wood |
| 7,331,348 | B1 * | 2/2008 | Beevers ................... 128/207.18 |
| 7,337,780 | B2 | 3/2008 | Curti et al. |
| 7,406,966 | B2 * | 8/2008 | Wondka ................... 128/207.18 |
| 2006/0180151 | A1 | 8/2006 | Rinaldi |
| 2008/0319435 | A1 * | 12/2008 | Rioux et al. .................... 606/33 |

* cited by examiner

*Primary Examiner* — Jason Flick
*Assistant Examiner* — Brooke Matney
(74) *Attorney, Agent, or Firm* — Kelley Drye & Warren, LLP

(57) ABSTRACT

An embodiment of the present invention is a nasal cannula for delivering continuous positive airway pressure ("CPAP") to a patient's nares during operative procedures or in critical care areas. A malleable metal or plastic is encased in the bridge of the cannula to allow it to be shaped to the patient's face. As a result of contouring the cannula to the face, air leaks are minimized allowing a seal to be provided when an op site is applied to cover the upper lip, nasal cannula and nose. The cannula's nasal inserts can end in nontapered or slightly tapered non-sealing beads, which may be slightly angled out to accommodate various facial anatomies. When approximately several liters per minute of oxygen are flowed through the cannula, CPAP is obtained.

12 Claims, 5 Drawing Sheets

NASAL CANNULA ASSEMBLY

CROSS-REFERENCE TO RELATED APPLICATIONS

The present invention relates to, and is entitled to the benefit of the earlier filing date and priority of, U.S. Application No. 61/157,440 filed on Mar. 4, 2009, which is herein incorporated by reference as if fully set forth.

BACKGROUND OF THE INVENTION

Continuous nasal positive airway pressure or continuous positive airway pressure ("CPAP") has been used to treat a variety of diseases including sleep apnea. Most devices used to treat sleep apnea are expensive, cumbersome and designed for repeat use; therefore, they are not used in the operating room, emergency room, or critical care areas. During sedative anesthesia using nasal cannula to deliver oxygen, it is not uncommon for the patient's airway to obstruct as in sleep apnea and for the patient to become hypoxic. This is more marked during procedures in which the upper airway is shared with the surgeon or endoscopist. Various maneuvers such as delivering high oxygen flow rates or jaw thrusts have been used to overcome the obstruction with varying success. Occasionally, endotracheal intubation or canceling and postponing the procedure are necessary.

What is needed in the industry is a nasal cannula that can be contoured to each patients face, providing nasal inserts that are long enough to rest inside the patients nares, flared at the ends to provide a loose seal and covering the tubing and nasal facial area with a transparent dressing, enabling nasal CPAP to be obtained, improving oxygenation. Such a device would overcome the inherent problem of existing nasal cannulae, which are designed to loosely fit in the nares and cannot easily contour to the face making it difficult to provide a seal and nasal CPAP.

A number of inventions have been proposed to allow contouring or adhering the cannula to the upper lip, widening the nasal inserts to provide a complete seal for providing CPAP or just securing the nasal cannula by an adherent dressing. None of these approaches has solved the problems—discussed.

U.S. Pat. No. 3,513,844 issued on May 26, 1970 to Smith describes a nasal cannula having a metal insert between the nostril conduits to permit manual shaping and contouring to the upper lip. The metal insert is attached to the outside of the cannula and is not incorporated into the bridge. Unlike the present invention where it is necessary for the bridge to extend beyond the upper lip to both cheek areas to provide as much of an airtight fit as possible, the Smith cannula bridge does not extend beyond the upper lip.

U.S. Pat. No. 4,278,082 issued on Jul. 14, 1981 to Blackmer describes a nasal cannula where the two-formed ends of the cannula are attached to a metal bridge, which spans the distance between the narine tubes and may be shaped to provide a more comfortable fit.

U.S. Pat. No. 5,513,635 issued on May 7, 1996 to Bedi describes an adhesive dressing applied to the nose with extensions that wrap around the cannula. The purpose is to secure the cannula to the nose without covering the nostrils.

U.S. Pat. No. 5,682,881 issued on Nov. 4, 1997 to Winthrop et al describes a nasal cannula CPAP device which uses adhesive foam strips attached to the outside of the body of the cannula to secure it to the upper lip to hold it in position under the nose.

Nasal CPAP devices with various means to completely seal the nares have been described in U.S. Pat. Nos. 4,648,498, 5,269,296, 6,431,172, 7,047,974, and 7,188,624. These patents use various materials and shapes such as silicone, foam or inflatable cushions all with the intent to seal the nares to provide CPAP. Use of these approaches have been shown to irritate or otherwise damage the inside of the nares. The present invention does not use an approach wherein the cannula completely seals the nares.

Tse et al describe the use of a clear plastic sheet placed over the face of a patient and taped to their head during upper endoscopy and other sedative procedures. The nasal cannula effectively becomes a face tent providing an oxygen reservoir increasing the inspired oxygen concentration and patient oxygenation. Unfortunately, this is somewhat cumbersome to apply, may be anxiety provoking and may impede the performing the operative procedure. This approach also does not lend itself to use in the emergency room or other critical areas.

In contrast to other nasal CPAP devices, embodiments of this invention employ unique approaches to seal the nostrils to create positive nasal airway pressure to overcome upper airway obstruction while being easily and quickly applied to the patient, economical, disposable, and would be available for use in a wide variety of settings.

What is needed in the industry is a device to provide CPAP comprising soft ovoid nasal inserts covering the end of the delivery tubes designed not to completely seal the nostrils, but to partially seal them. This decreases nasal mucosa irritation, facilitates patient comfort and acceptance, and increases ease of insertion and removal of the cannula while still decreasing the amount of entrained room air.

What is needed in the industry is a device to provide CPAP comprising a cannula softly encasing a malleable metal or plastic bar inside the bridge of the nasal cannula that extends to contour to both sides of the face. This allows the bridge of the nasal cannula to contour to the area of the face at the upper lip and continuing to the side of the nose. The nasal inserts may be angled slightly outward to allow contouring to a variety of anatomies when the semi rigid metal bar is shaped to the face.

What is needed in the industry is a device to provide CPAP comprising an anatomically shaped op site or Tegaderm dressing shaped to fit the nose and upper lip and areas just to the sides of the nose. This provides a complete seal to the nares to provide nasal CPAP.

What is needed in the industry is a device to provide CPAP comprising an option so that the design of the end of the cannula can be fit inside a special nasal airway. This could be useful during longer surgeries where access to the airway may be impeded and where a patient with a difficult airway may require sedation for several hours.

Embodiments of the present invention overcome one or more of these limitations of known devices by creating a novel and non-obvious nasal cannula that can be contoured to each patients face, providing nasal inserts that are long enough to rest inside the patients nares, and in one embodiment, flared at the ends to provide a loose seal, and covering the tubing and nasal facial area with a transparent dressing, to permit nasal CPAP to be obtained and improving oxygenation. This overcomes the inherent problems of existing nasal cannulae, which are designed to loosely fit in the nares and cannot easily contour to the face making it difficult to provide a seal and nasal CPAP or fit tightly in the nares, thereby irritating the nasal mucosa.

Embodiments of the present invention are designed to overcome one or more of the limitations of currently known devices. These, as well as other objects and advantages of the present invention will be better understood from the detailed description and accompanying drawings.

SUMMARY OF THE INVENTION

Responsive to the foregoing challenges, Applicant has developed an innovative system and method for providing CPAP in patients while overcoming some of the limitations of known devices. An embodiment of the present invention is a nasal cannula assembly comprising a formable bridge, at least one nasal insert, at least one gas supply tube, a shape-retaining malleable element disposed in the bridge, and an op site dressing, wherein the gas supply tube is in communication with the bridge, the bridge is in communication with the nasal insert, and the op site dressing is in communication with the bridge. The malleable material may be a metal and/or a plastic. The nasal insert may be slightly flared and/or comprise a non-compressible bead disposed on the nasal insert. The op site dressing may comprise an adhesive backing.

An embodiment of the present invention is a nasal cannula assembly comprising a formable bridge comprising a first end, a second end, and a middle portion disposed between the first and second ends, wherein the formable bridge comprises a channel extending from the first end to the second end through the middle portion, at least one nasal insert disposed on the middle portion of the formable bridge in fluid communication with the channel and comprising a non-compressible bead disposed on an exterior surface of the nasal insert, at least one gas supply tube in fluid communication with the channel at the first or second end of the formable bridge, a shape-retaining malleable element in communication with the middle portion of the formable bridge, and an op site dressing comprising an adhesive backing in communication with the formable bridge.

An embodiment of the present invention is a method of providing continuous positive airway pressure to a patient in need thereof, comprising the steps of fitting on the patient a nasal cannula assembly, the assembly comprising a formable bridge comprising a first end, a second end, and a middle portion disposed between the first and second ends, and a channel extending from the first end to the second end through the middle portion, two nasal inserts disposed on the middle portion of the formable bridge in fluid communication with the channel, at least one gas supply tube in fluid communication with the channel at the first or second end of the formable bridge, a shape-retaining malleable element in communication with the middle portion of the formable bridge, and an op site dressing comprising an adhesive backing in communication with the formable bridge, and administering a gas to the patient through the nasal cannula assembly.

It is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention and, together with the detailed description, serve to explain the principles of the present invention.

BRIEF DESCRIPTION OF THE DRAWINGS

In order to assist in the understanding of this invention, reference will now be made to the appended drawings, in which like reference characters refer to like elements.

DETAILED DESCRIPTION OF THE INVENTION

Reference will now be made in detail to embodiments of the present invention, examples of which are illustrated in the accompanying drawings. An embodiment of the present invention is a nasal cannula assembly designed to deliver continuous positive airway pressure ("CPAP") to improve oxygenation during spontaneous ventilation in the operating, procedure room, or critical care area by sealing off the nostrils from outside air and by providing a mechanism to allow the nasal cannula to conform to the patient's facial anatomy to facilitate a complete seal. The device is designed to be easy and quick to apply, comfortable for the patient and relatively inexpensive.

In contrast to other nasal CPAP devices, embodiments of the present invention use unique approaches to seal the nostrils to create nasal CPAP to overcome upper airway obstruction while being easily and quickly applied to the patient.

Unlike other CPAP devices, an embodiment of the present invention comprises soft ovoid nasal inserts covering the end of the delivery tubes designed not to completely seal the nostrils but to partially seal them. This decreases nasal mucosa irritation, facilitates patient comfort and acceptance, and increases ease of insertion and removal of the cannula while still decreasing the amount of entrained room air.

Unlike other CPAP devices, an embodiment of the present invention comprises a cannula softly encasing a malleable metal or plastic bar inside the bridge of the nasal cannula that extends to contour to both sides of the face. This allows the bridge of the nasal cannula to contour to the area of the face at the upper lip and continuing to the side of the nose. The nasal inserts may be angled slightly outward to allow contouring to a variety of anatomies when the semi rigid metal bar is shaped to the face.

Another unique aspect of an embodiment of the present invention is the use of an anatomically shaped op site or Tegaderm dressing shaped to fit the nose and upper lip and areas just to the sides of the nose. This provides a substantially complete seal to the nares to provide nasal CPAP. A substantially complete seal is defined as the seal necessary to achieve CPAP in the patient.

One embodiment of the present invention can be optioned so that the design of the end of the cannula can be fit inside a special nasal airway. This could be useful during longer surgeries where access to the airway may be impeded and where a patient with a difficult airway may require sedation for several hours.

Figure 1:
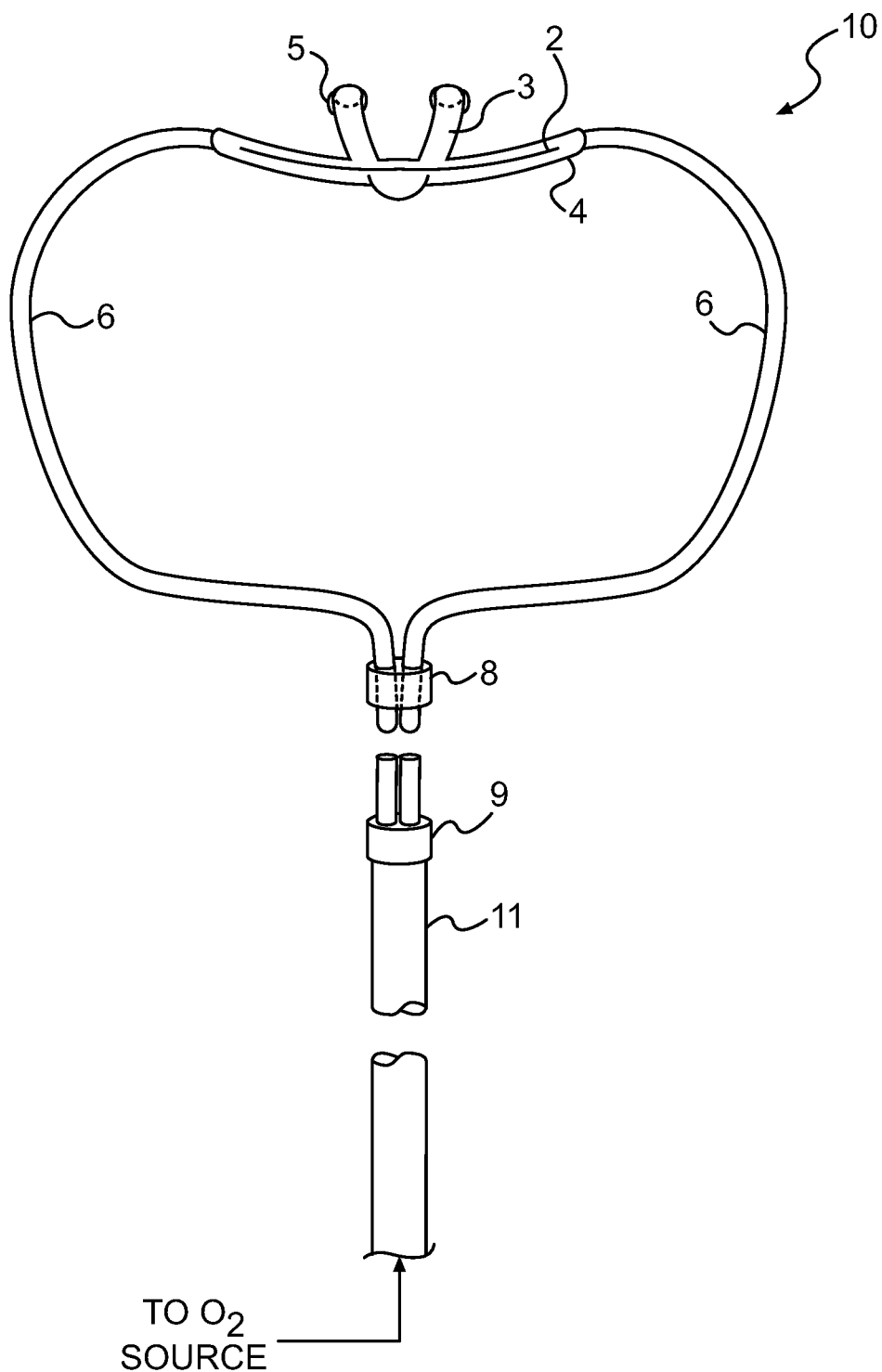
FIG. 1 is an elevational view of a nasal harness including a nasal cannula as embodied in the present invention, minus the op site.
Figure 2:
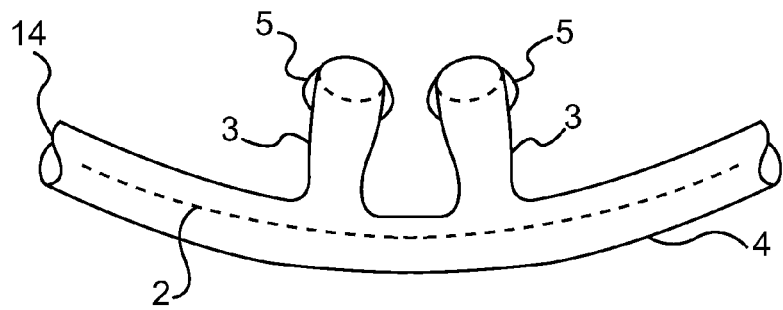
FIG. 2 is a projection of the cannula body with the nasal inserts in isolation.

As shown in FIG. 1 and FIG. 2, an embodiment of the present invention consists of nasal cannula assembly 10 in communication with a source of gas, such as, but not limited to, oxygen. Nasal cannula assembly 10 comprises formable bridge 4, at least one, and preferably two, nasal inserts 3, at least one, and on some embodiments two, gas supply tubes 6, and op site dressing 12. Bridge 4 further comprises a shape-retaining malleable element 2 disposed within or on an exterior surface of bridge 4. Bridge 4 may be a plastic or metal reinforced bridge, or comprised of any other suitable material. Bridge 4 may be in communication with at least one, and generally a pair of nasal inserts 3. Nasal inserts 3 may comprise enlarged tips 5. Nasal inserts 3 are in communication with bridge 4 and gas supply tubes 6. Gas supply tubes 6 are in communication with common connector 9 which is sealingly connected to one end of common gas supply tube 11. The complete assembly may be held in place by any convenient or conventional construction such as, but not limited to, slip ring 8.

Figure 3A:
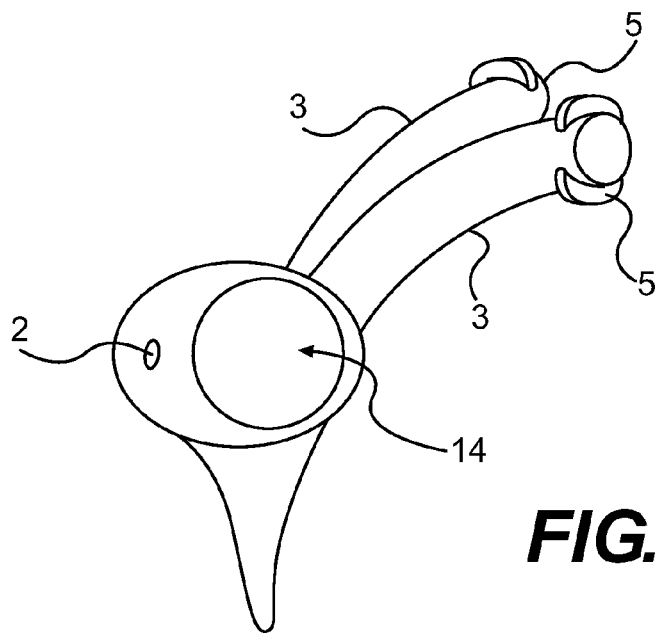
FIG. 3 is a cross section area of the cannula body and nasal inserts where it contacts the nose and face.
Figure 3B:
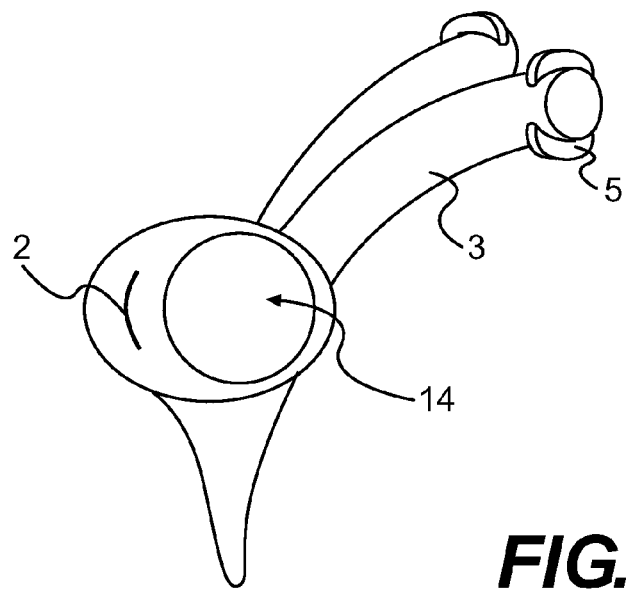

As shown in FIGS. 3A and 3B, malleable element 2 may be a solid or hollow tube, ribbon, band, round or flat, or may be of any other suitable shape. Malleable element 2 may be comprised of metal, including, but not limited to, steel, aluminum, or any other suitable shape-retaining metal, or plastic (for use in MRI), or any other suitable non-metallic shape-retaining material. Malleable element 2 in an example embodiment may be approximately 1 mm diameter. Malleable element 2 may extend as one continuous member, such as a tube or ribbon, from approximately the center of bridge 4 up to approximately 2 cm to 8 cm, and preferably approximately 5 cm on each side extending outward from approximately the center of bridge 4. Malleable element 2 and oxygen supply tube 6 disposed inside bridge 2 are separated but may be jointly encased in a soft silicon/plastic or any other suitable material to allow bridge 4 to be comfortably contoured to the face of a patient. Supply tubes 6 are in continuity and fluid communication and supply oxygen to nasal inserts 3. In one embodiment nasal inserts 3 that extend into the nostrils may be slightly angulated outward so that when bridge 4 is compressed to fit the face they lie inside the patient's nose. Nasal inserts 3 may be slightly elongated and enlarged at tips 5 to provide a better seal in the nose but are not intended to provide a complete seal. Tip 5 may be comprised of a compressible, or preferably, a non-compressible bead, or any other suitable shape. This helps to preclude irritation of the nasal mucosa and patient discomfort.

Figure 4:
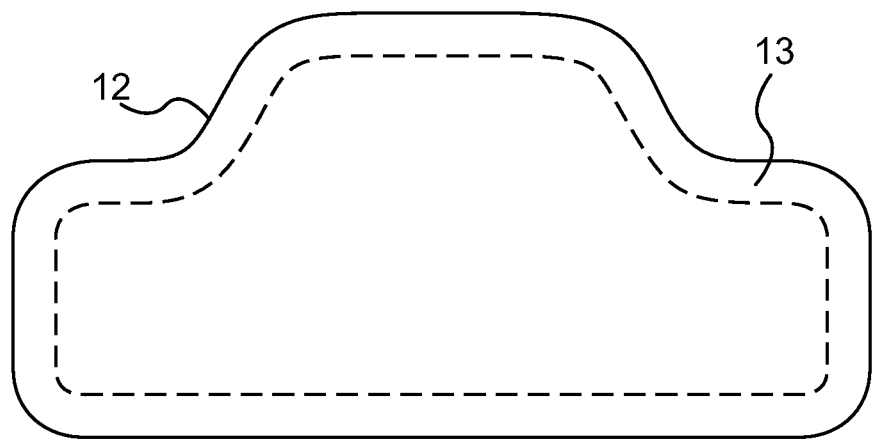
FIG. 4 is a projection of the op site in isolation.

In FIG. 4, op site dressing 12 may be configured to fit the area around the patient's nose and can be easily applied. Op site 12 is designed to create a seal enclosing bridge 4 and nasal inserts 3 when op site 12 is applied to the patient. The seal is sufficient to enable CPAP when a certain volume of gas is delivered to nasal inserts 3. In one embodiment paper-reinforced borders 13 surround the perimeter of op site 12. The final shape or shapes and size of op site 12 may vary. It is envisioned that in one embodiment more than one shape and/or size may be supplied.

Figure 5:
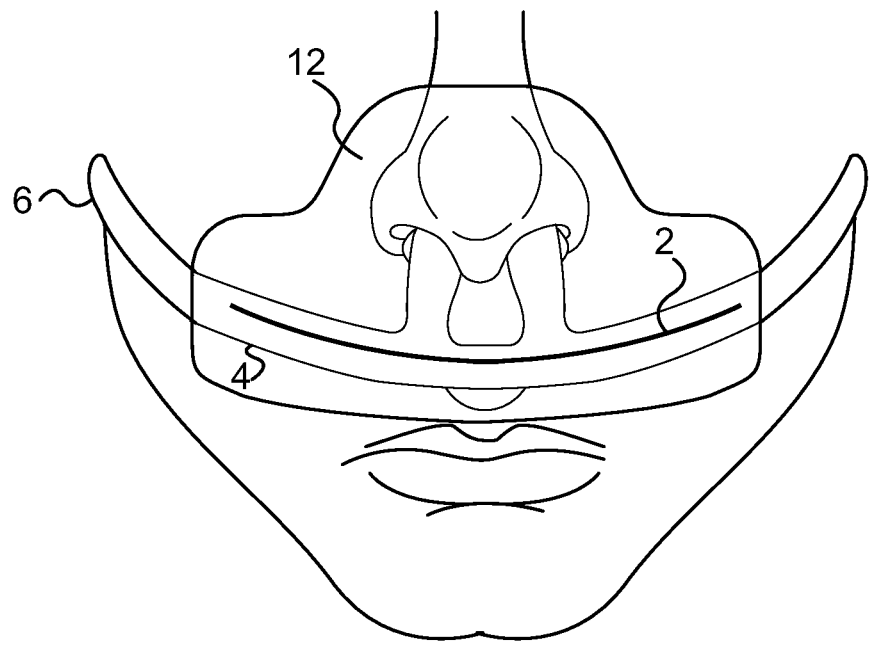
FIG. 5 is a schematic representation of the cannula and the op site on the head of a user, frontal view.

FIG. 5 illustrates an embodiment wherein op site 12 is shaped to avoid or minimize contact with the patient's eyes when in use.

Figure 6:
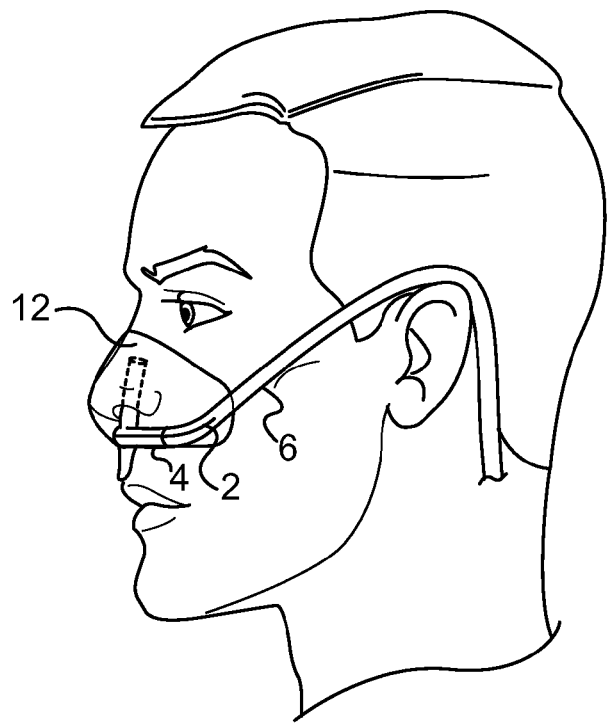
FIG. 6 is a schematic representation of the cannula and the op site on the head of a user, side view.

FIG. 6 illustrates how bridge 4 and op site 12 contours and extends beyond the patient's nose to the side of the face and the nasolabial area to seal the nares from room air.

Figure 7:
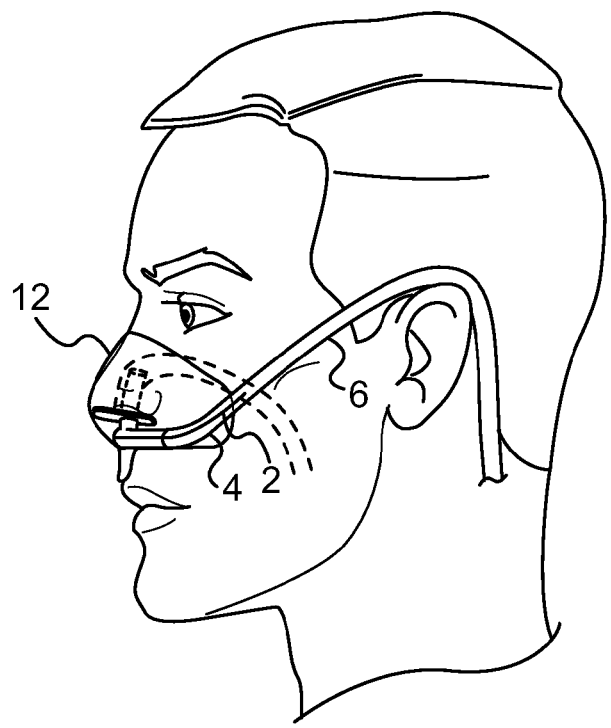
FIG. 7 is a schematic representation of a variant of the present cannula where either nasal insert can fit into a nasal airway to further obviate any obstruction and provide nasal CPAP.
Figure 8:
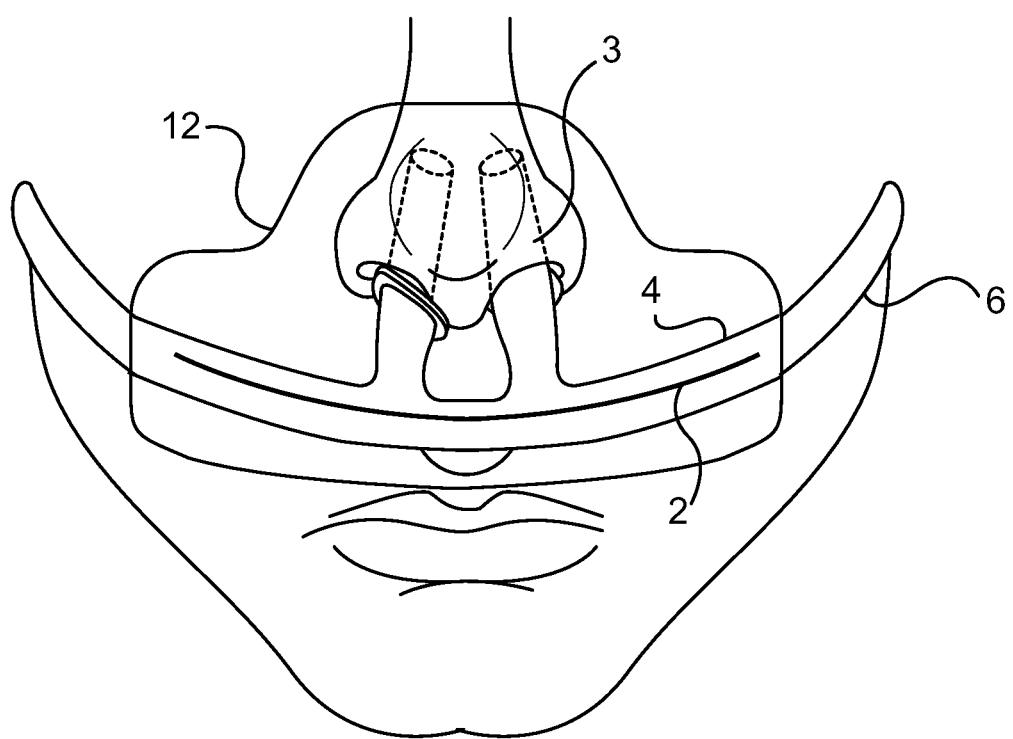
FIG. 8 is a schematic representation of a variant of the present cannula where either nasal insert can fit into a nasal airway to further obviate any obstruction and provide nasal CPAP.

FIG. 7 and FIG. 8 illustrate one embodiment of the present invention comprising bridge 4 constructed with non-flared nasal inserts 3. Non-flared nasal inserts 3 are constructed to allow them to fit into a nasal airway or in a nare. The figures show one of non-flared nasal inserts 3 inserted into a nasal airway residing in a nare, while the other nasal insert 3 is inserted into the other nare. Op site 12 covers the area as previously discussed.

In an example embodiment, bridge 4 comprises a first end, a second end, and a middle portion disposed between the first and second ends. Channel 14 is disposed within bridge 4 extending from an opening in the first end to an opening in the second end, forming a single continuous channel through the middle portion of bridge 4. Channel 14 openings at the first and second ends of bridge 4 are in communication with gas supply hose(s) 6. Nasal inserts 3 are disposed in or near the middle portion of bridge 4, and are in fluid communication with channel 14 in bridge 4. Gas supplied through supply hose(s) 6 is delivered to nasal inserts 3 through channel 14. Malleable element 2 is also disposed in, on, or about bridge 4. Malleable element 2 may be a single continuous element, or two or more discontinuous elements, extending from at or near the middle portion of bridge 4 outward towards the first and second ends of bridge 4. Malleable element 2 need not extend all the way to the first or second end of bridge 4, and may be disposed anterior, posterior, or in any one position, or more than one position relative to channel 14 and the patient. Malleable element 2 is operable to form to the exterior features of a patient's face, and may be shape-retaining in character.

An embodiment of the present invention is a method of providing continuous positive airway pressure to a patient in need thereof, comprising the steps of fitting on the patient a nasal cannula assembly 10, assembly 10 comprising formable bridge 4 comprising a first end, a second end, and a middle portion disposed between the first and second ends, and channel 14 extending from the first end to the second end through the middle portion, two nasal inserts 3 disposed on the middle portion of formable bridge 4 in fluid communication with channel 14, at least one gas supply tube 6 in fluid communication with channel 14 at the first or second end of formable bridge 4, a shape-retaining malleable element 2 in communication with the middle portion of formable bridge 4, and an op site dressing 12 comprising an adhesive backing in communication with formable bridge 4 and the patient, and administering a gas to the patient through the nasal cannula assembly 10.

It will be apparent to those skilled in the art that variations and modifications of the present invention can be made without departing from the scope or spirit of the invention. Thus, it is intended that the present invention cover all such modifications and variations of the invention, provided they come within the scope of the appended claims and their equivalents.

What is claimed is:
1. A nasal cannula assembly comprising:
a formable bridge comprising a first end, a second end, and a middle portion disposed between the first and second ends, wherein the formable bridge comprises a channel extending from the first end to the second end through the middle portion,
at least one nasal insert disposed on the middle portion of the formable bridge and in fluid communication with the channel, wherein the nasal insert does not completely seal the patient's nares from room air,
at least one gas supply tube in fluid communication with the channel at the first or second end of the formable bridge,
a shape-retaining malleable element in communication with the middle portion of the formable bridge, and
an op site dressing disposed over and covering the nasal insert and the formable bridge and extending beyond the patient's nose to the side of the face and the nasolabial area providing a substantially complete seal to the patient's nares from room air.

2. The assembly of claim 1, wherein the malleable element is metal.

3. The assembly of claim 1, wherein the malleable element is plastic.

4. The assembly of claim 1, wherein the nasal insert is slightly flared.

5. The assembly of claim 1, comprising a non-compressible bead disposed on the nasal insert.

6. The assembly of claim 1, wherein the op site dressing comprises an adhesive backing.

7. The assembly of claim 1, comprising two nasal inserts, wherein the two nasal inserts are substantially parallel to one another when the nasal cannula assembly is in use.

8. A nasal cannula assembly comprising:
a formable bridge comprising a first end, a second end, and a middle portion disposed between the first and second ends, wherein the formable bridge comprises a channel extending from the first end to the second end through the middle portion,
at least one nasal insert disposed on the middle portion of the formable bridge in fluid communication with the channel and comprising a non-compressible bead disposed on an exterior surface of the nasal insert, wherein the non-compressible bead does not completely seal the patient's nares from room air,
at least one gas supply tube in fluid communication with the channel at the first or second end of the formable bridge,
a shape-retaining malleable element in communication with the middle portion of the formable bridge, and
an op site dressing comprising an adhesive backing disposed over and covering the nasal insert and the formable bridge and extending beyond the patient's nose to the side of the face and the nasolabial area providing a substantially complete seal to the patient's nares from room air.

9. The assembly of claim 8, wherein the malleable element is metal.

10. The assembly of claim 8, wherein the malleable element is plastic.

11. The assembly of claim 8, wherein the nasal insert is slightly flared.

12. A method of providing continuous positive airway pressure to a patient in need thereof, comprising the steps of:
fitting on the patient a nasal cannula assembly, the assembly comprising a formable bridge comprising a first end, a second end, and a middle portion disposed between the first and second ends, and a channel extending from the first end to the second end through the middle portion, two nasal inserts disposed on the middle portion of the formable bridge in fluid communication with the channel wherein the nasal inserts do not completely seal the patient's nares from room air, at least one gas supply tube in fluid communication with the channel at the first or second end of the formable bridge, a shape-retaining malleable element in communication with the middle portion of the formable bridge, and an op site dressing comprising an adhesive backing disposed over and covering the nasal insert and the formable bridge and extending beyond the patient's nose to the side of the face and the nasolabial area providing a substantially complete seal to the patient's nares from room air, and
administering a gas to the patient through the nasal cannula assembly.

* * * * *